United States Patent [19]

Thornton

[11] 4,335,071
[45] Jun. 15, 1982

[54] PRESSURE-VACUUM PURGE CYCLE

[75] Inventor: David C. Thornton, Erie, Pa.

[73] Assignee: American Sterilizer Company, Erie, Pa.

[21] Appl. No.: 194,690

[22] Filed: Oct. 6, 1980

[51] Int. Cl.³ ................................................. A61L 2/06
[52] U.S. Cl. ...................................... 422/26; 422/33; 422/116
[58] Field of Search ....................... 422/26, 27, 33, 116

[56] References Cited

U.S. PATENT DOCUMENTS

| | | | |
|---|---|---|---|
| 3,409,389 | 11/1968 | Bjork | 422/26 |
| 3,436,170 | 4/1969 | Lodge | 422/26 |
| 3,494,725 | 2/1970 | Irons et al. | 422/26 |
| 4,203,943 | 5/1980 | Gillis et al. | 422/27 |
| 4,203,947 | 5/1980 | Young et al. | 422/26 X |
| 4,241,010 | 12/1980 | Baran | 422/27 X |

Primary Examiner—Barry S. Richman
Attorney, Agent, or Firm—Robert D. Yeager

[57] ABSTRACT

A pressure-vacuum purge cycle that is employed in the sterilization of dry goods and especially of wrapped fabric packs employs a positive pressure steam pulse followed by a positive pressure steam displacement of continuously vented air in novel combination with subsequent vacuum pulsing at limited maximum negative pressures to provide improved conditioning of the said goods in respect of the purging of air and moisturizing of the goods and improved economies in time and energy consumption.

2 Claims, 1 Drawing Figure

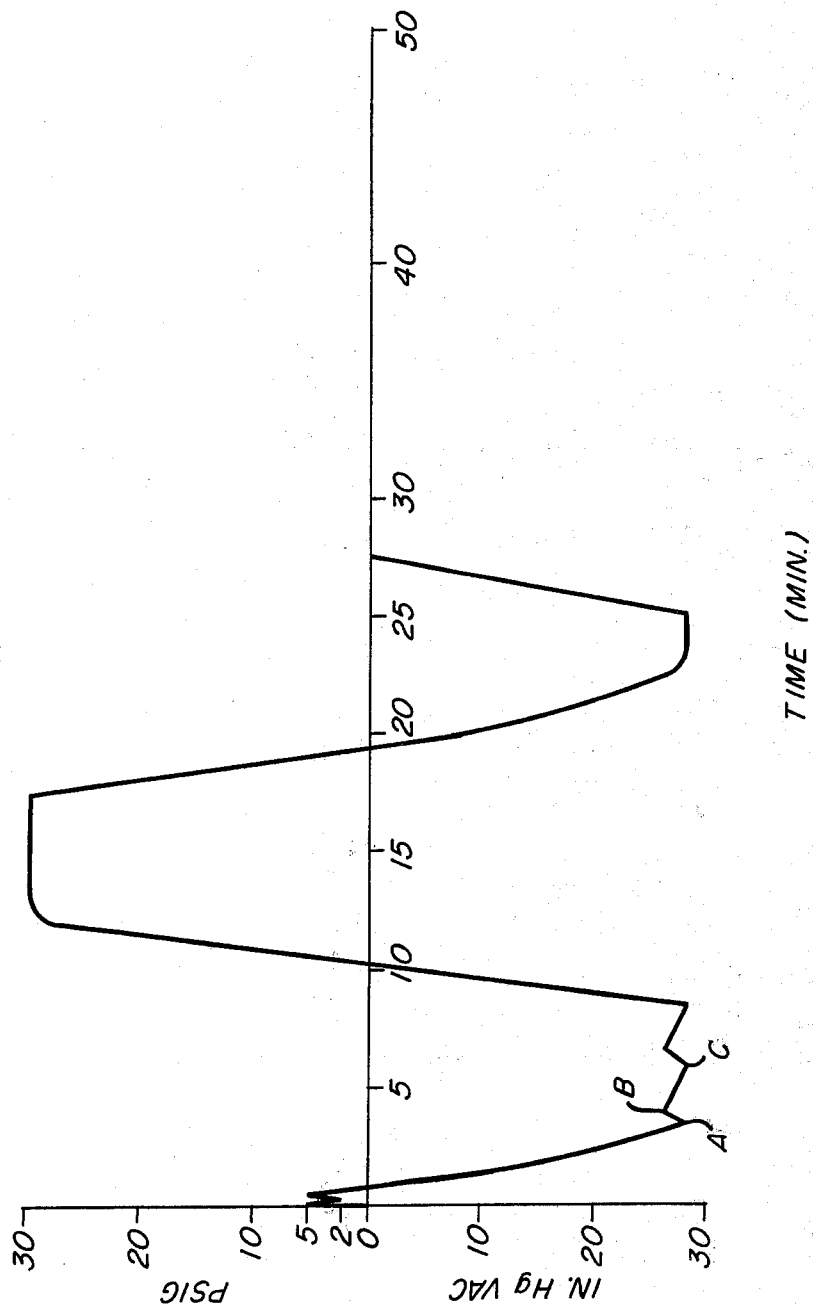

PRESSURE-VACUUM PURGE CYCLE

BACKGROUND OF THE INVENTION

1. Field of the Invention

This invention relates to cycles for use in steam sterilization.

2. Description of the Prior Art

Various cycles have been designed for steam and ethylene oxide gas sterilization as it is used in hospitals and laboratories. These cycles may be characterized by the medium used; for example a steam cycle or ethylene oxide gas cycle; or by the nature of the fluid flow therein, such as a gravity cycle. Cycles in this art are also designated by the nature of the load; for example, a vacamatic cycle is one for a load of wrapped fabric goods such as bedding or linens; and a liquid cycle is used when liquids are being sterilized.

For descriptive purposes a steam or gas cycle may also be divided into four functional steps: (i) removing air from the chamber; (ii) removing air from the load and humidifying the load; (iii) exposing the load, or actual sterilization of the load and (iv) drying the load. In the art, step (ii) is also termed "conditioning" the load.

The conditioning phase, which removes air from the load and moisturizes the load, is particularly important to the sterilization process. Moist heat in the form of saturated steam kills microorganisms by thermal destruction and heat denaturation of microbial cell proteins. Direct steam contacts the cell, condensation occurs, and the latent heat of vaporization is discharged. When moisture is present, coagulation takes place at relatively lower temperatures; but when no moisture is present, higher temperatures are required. Hot air alone, not carrying this latent heat, is not an effective sterilant, and may also damage a load, such as fabric because of the high temperatures required. It is essential to effective sterilization that moist heat penetrate the load and contact all surfaces; any air present will impede sterilization. Thus it is critical to remove substantially all air from the chamber and the load, as well as to humidify and moisturize the load. Chamber air may generally be adequately removed by drawing a vacuum in the chamber (0–¾ inch mercury). However it is more difficult to remove air from a load, particularly a wrapped fabric (vacamatic) load, because the air becomes trapped therein. Conditioning therefore becomes especially critical for vacamatic cycles.

A steam sterilization cycle is essentially a combination of the use of steam and/or vacuum in a pressure chamber to sterilize the load therein. It is known in steam sterilization cycles to use the gravity displacement of air in the chamber by steam for the aforesaid steps (i) and (ii). It is also known to use what is known in the art as "pulsing", which may be commonly employed for step (ii). Pulsing is the process of increasing chamber pressure to a maximum pressure, generally by admission of steam; followed by decreasing sterilizer pressure to a minimum pressure (by drawing a vacuum and/or shutting off steam) to a minimum pressure preceding the next pulse.

Pulsing has proven to be an effective means of conditioning a load for sterilization, however generally requires a high energy consumption in terms of steam requirements and the use of vacuum pumps. Gravity air displacement, on the other hand, is energy efficient; however it is prohibitively time consuming and does not remove chamber air as efficiently as a vacuum pump. Vacuum/steam cycles without pulsing do not always adequately condition a load for proper sterilization. While combinations of these processes have been employed in the art they have been subject to the aforesaid limitations; they either have a high steam consumption, or vacuum pump energy demand, require excessive time to complete the cycle, or result in inadequate sterilization for certain types of loads.

SUMMARY OF THE INVENTION

The conditioning step of this invention can be integrated into any standard sterilization cycle to give an improved conditioning process; and thereby a sterilization cycle which achieves maximum energy efficiency and maximum sterilization efficiency in a minimum of time. The conditioning step of the invention comprises the steps of: (i) introducing steam into a sterilization chamber by at least one positive pressure pulse having a predetermined positive pressure at which steam and air will stratify and said steam will thereby displace said air in said chamber in a predetermined time; (ii) terminating said introduction of steam and substantially simultaneously applying vacuum means to obtain a vacuum of no less than 26 inches of mercury, and terminating said application of vacuum means and substantially simultaneously commencing at least two predetermined vacuum pulses for a predetermined time. This improved conditioning phase is optimal for a dry-goods-load steam sterilization cycle and particularly for a vacamatic (wrapped goods) cycle; it removes air from a chamber and a load, and humidifies the load with maximum energy and cycle efficiency.

DETAILED DESCRIPTION OF THE PREFERRED EMBODIMENTS

The conditioning step or phase of the present invention minimizes energy consumption as well as time periods required for sterilization while still achieving adequate sterilization. While the conditioning phase may be used with any conventional cycle within the spirit and scope of the invention, it provides excellent results with vacamatic cycles which as discussed above are particularly difficult to sterilize. The conditioning phase will therefore be discussed in the nonlimiting example of a vacamatic steam sterilization cycle.

In the initial step of the conditioning phase, as shown in the single FIGURE, steam is introduced into a sterilization chamber at a predetermined positive pressure, which is one at which steam and air will stratify and the steam will thereby displace air in the chamber in a predetermined time.

The purpose of this step is to create an energy-efficient air removal in the chamber without creating turbulence, while using as little steam as possible. 5 psig is an optimum predetermined positive pressure which can obtain these results, and when used with pulsing, described in greater detail below, air-steam stratification occurs which further increases the efficiency of air removal from the chamber. As shown in Table I below, the time for removing air, the amount of air remaining, and the energy expended, are decreased significantly when using steam displacement at these selected pressures, compared to conventional removal of chambered air by deep vacuum.

TABLE I

| Air Removal Method | Chamber Volume (ft.$^3$) | Required Time (Vacuum) | Energy Expended (Watt-hr.) | % Air Remaining |
|---|---|---|---|---|
| Deep Vacuum-1 HP Liquid Ring | 8 | 10 min. (87 mm Hg abs) (8/2/79) | 120 | 11.5 |
| Deep Vacuum-1 HP Air Ejector | 8 | 11 min. (100 mm Hg abs) | 132 | 13.2 |
| Steam Displacement | 8 | ½ min. (27 mm Hg abs) | 113 | <3.7 |

The steam displacement shown in Table I was operated by opening the drain (a sized orifice) and feeding low pressure steam (2–5 psig) into the chamber for thirty seconds. The predetermined time, in the instant example thirty seconds, is determined by chamber volume and steam transducer calculations. The predetermined time is therefore determined by the amount of steam needed to displace the air in the particular chamber used, in the instant case an eight cubic foot chamber.

This initial steam input is introduced as a positive pressure pulse. A positive pulse is herein defined as increasing sterilizer pressure to a maximum pressure followed by decreasing sterilizer pressure to a minimum pressure preceeding a next pulse; which maximum and minimum pressures are above atmospheric pressure. The maximum positive pressure is the high pulse point; and the minimum positive pressure is the low pulse point as shown in the FIGURE. Pressure is increased to maximum by admission of steam and pressure is decreased to minimum by venting (through the drain orifice) and termination of steam. It is essential that the positive pressure pulse(s) of the present invention be at those pressures at which steam and air will stratify; the optimum range, as shown in the drawing, is a range of 2–5 psig. Tests have shown that little mixing occurs at 5 psig and with the steam being shut off down to 2 psig the steam has a chance to stratify pushing the air out of the chamber to exhaust in the bottom (drain). Steam, at 5 psig and 228° F., weighs 0.05 lg.$_m$/ft.$^3$, while air at the same pressure and temperature weighs 0.078 lb.$_m$/ft.$^3$, or 56 percent more. Furthermore, if the air in the chamber is still 70° F. (i.e. essentially at room temperature before beginning the process, the density is now 0.1 lb.$_m$/ft.$^3$ or 100 percent more than the density of the incoming steam in the 5 psig chamber pressure range.

While at least one such positive pressure pulse, preferably having as shown in the drawing a maximum positive pressure of 5 psig and a minimum positive pressure of 2 psig, is required, three positive pressure pulses may be used. The positive pressure pulses, as discussed above, are applied for the calculated predetermined time (in the instant case thirty seconds) needed to remove all the air in the chamber by steam displacement. As also stated above, increase to the maximum positive pressure of 5 psig is obtained by admission of steam, and reduction to the minimim positive pressure of 2 psig is achieved by shutting off steam to the chamber. The drain remains open during the entire conditioning phase and sterilization cycle. During the air removal portion of the cycle (when the positive pressure pulse is being applied), displaced air vents through the drain orifice.

Steam is shut off at the end of the positive pressure pulse(s), and vacuum means are substantially simultaneously applied to the chamber to obtain a vacuum of no less than 26 inches of mercury. The vacuum means are terminated while substantially simultaneously applying at least two predetermined vacuum pulses. A vacuum pulse, as herein used, is a pulse at negative pressure or below atmospheric pressure (vacuum). A vacuum pulse, as shown in the drawing, is read inversely (i.e. pressure is increased while vacuum is decreased). Thus, the high point of the pulse, which would correspond to the maximum positive pressure, is actually the minimum negative pressure; while the low point of the pulse (the minimum positive pressure) is the maximum negative pressure. Negative pressure in the vacuum pulses of the conditioning phase is increased by applying a vacuum pump, and decreased by admission of steam with the vacuum pump shut off. Each of the vacuum pulses as herein used comprises: (i) admitting steam for twenty seconds to a minimum negative pressure of no less than 20 inches of mercury and (ii) terminating said steam while substantially simultaneously applying vacuum means for a period of no less than two minutes to obtain a maximum negative pressure of no less than 26 inches of mercury. The minimum negative pressure of 20 inches of mercury represents the greatest degree of vacuum needed to obtain air removal from the load (a wrapped fabric load), while the admission of steam for 20 seconds represents the amount of steam in terms of time at that particular (negative) pressure to moisturize a load. Use of more steam while effectively conditioning, will dissipate the energy saving advantages of the cycle. Use of less steam (in terms of time) will not sufficiently condition the load. Similarly a vacuum of less than 20 inches of mercury (the critical limit), will be insufficient to effect conditioning. While a vacuum of greater than 20 inches of mercury can be drawn this will increase the time it takes to run the cycle as well as increasing the energy consumption. In relation to the critical lower limit of 20 inches of mercury, an optimum maximum negative pressure (or vacuum) of about 26 inches may be used without wasteful consumption of energy; this limit represented in the drawing as the low point of the pulse. A minimum negative pressure (or vacuum) of approximately 25 inches of mercury is shown in the drawing as the high vacuum pulse point. The aforesaid maximum negative pressure is achieved by applying vacuum means while substantially simultaneously shutting off steam, for a period of not less than two minutes. The critical lower limit for applying the vacuum means of two minutes represents the amount of time that the vacuum must be applied at the negative pressure to achieve adequate conditioning. Application of vacuum means for seven minutes yields improved conditioning results, but lessens the time efficiency of the cycle. Two minutes represents the optimum time as well as the critical lower limit for applying the vacuum means to achieve conditioning of the load while still maintaining time efficiency.

The vacuum pulse segment A, B, C of the cycle discussed above, will purge the center of the wrapped fabric pack with super-heated steam and draw the air out with it.

The conditioning phase is completed at the end of the vacuum pulses, and a standard sterilization exposure may be commenced by admitting steam to the appropriate positive pressure, (such as 30 psig) for an appropriate time period (such as four minutes) which accomplishes the actual thermal destruction of microorganisms, with steam penetrating the center of the load, and achieving sterilization.

In the final drying phase of the sterilization cycle a vacuum is drawn in the chamber and moisture is flashed into steam and drawn out of moisture absorbent loads. The use of the conditioning phase of the present invention not only reduces the overall time of the sterilization cycle, but uses significantly less steam consumption to achieve sterilization.

What is claimed is:

1. An improvement in the conditioning phase of a dry goods load sterilization cycle rendering maximum energy and cycle efficiency for use in a steam sterilization process, which conditioning phase removes air from a sterilization chamber and said load therein and humidifies said load, said improvement comprising the steps of:

introducing steam into said chamber above the air therein by at least one positive pressure pulse having a predetermined maximum positive pressure of about five pounds per square inch gauge and subsequently venting air therefrom to a predetermined minimum positive pressure of about two pounds per square inch gauge at both of which pressures steam and air will stratify and said steam will thereby displace said vented air in said chamber in a predetermined time;

terminating said introduction of steam and substantially simultaneously applying a vacuum of no less than 26 inches of mercury; and terminating said application of vacuum and substantially simultaneously commencing one of at least two predetermined vacuum pulses for a predetermined time.

2. The improvement recited in claim 1 wherein each of said predetermined vacuum pulses comprises:

admitting steam for 20 seconds to a minimum negative pressure of no less than 20 inches of mercury; and terminating said steam while substantially simultaneously applying vacuum means for a period of no less than 2 minutes to obtain a maximum negative pressure of no less than 26 inches of mercury.

* * * * *

UNITED STATES PATENT AND TRADEMARK OFFICE
CERTIFICATE OF CORRECTION

PATENT NO. : 4,335,071
DATED : June 15, 1982
INVENTOR(S) : David C. Thornton

It is certified that error appears in the above—identified patent and that said Letters Patent is hereby corrected as shown below:

Col. 2, line 26, delete ",", and substitute therefor --;--;

Col. 3, line 43, delete "1g", and substitute therefor --1b--;

Col. 4, line 49, delete "the" second occurrence, and substitute therefor --that--; and Col. 4, line 54, delete "critical lower", and substitute therefor --lower critical--.

Signed and Sealed this

Seventh Day of September 1982

|SEAL|

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,335,071
DATED : June 15, 1982
INVENTOR(S) : David C. Thornton

It is certified that error appears in the above—identified patent and that said Letters Patent is hereby corrected as shown below:

Col. 1, line 3, insert the following new paragraph:

--The Govenment has rights in this invention pursuant to Contract No. DAMD 17-79-C-9034 awarded by the United States Army.--

Signed and Sealed this

Twenty-second Day of November 1983

[SEAL]

Attest:

GERALD J. MOSSINGHOFF

Attesting Officer    Commissioner of Patents and Trademarks